(12) United States Patent
Yasunaga

(10) Patent No.: US 9,186,205 B2
(45) Date of Patent: Nov. 17, 2015

(54) SURGICAL TREATMENT SYSTEM

(71) Applicant: OLYMPUS CORPORATION, Tokyo (JP)

(72) Inventor: Shinji Yasunaga, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 322 days.

(21) Appl. No.: 13/761,628

(22) Filed: Feb. 7, 2013

(65) Prior Publication Data

US 2013/0150848 A1 Jun. 13, 2013

Related U.S. Application Data

(63) Continuation of application No. PCT/JP2011/071874, filed on Sep. 26, 2011.

(30) Foreign Application Priority Data

Sep. 27, 2010 (JP) ................. 2010-215961

(51) Int. Cl.
 *A61B 18/08* (2006.01)
 *A61B 18/14* (2006.01)
 *A61B 18/00* (2006.01)
(52) U.S. Cl.
 CPC ........... *A61B 18/1445* (2013.01); *A61B 18/085* (2013.01); *A61B 18/1447* (2013.01); *A61B 2018/0063* (2013.01); *A61B 2018/00994* (2013.01); *A61B 2018/1455* (2013.01)
(58) Field of Classification Search
 CPC ........... A61B 18/085; A61B 1208/087; A61B 18/1445; A61B 18/1447
 See application file for complete search history.

(56) References Cited

U.S. PATENT DOCUMENTS

2005/0090816 A1* 4/2005 McClurken et al. ............ 606/41
2005/0165444 A1* 7/2005 Hart et al. ..................... 606/213
(Continued)

FOREIGN PATENT DOCUMENTS

JP  62-219953 A  9/1987
JP  9-148053 A  6/1997
(Continued)

OTHER PUBLICATIONS

Chinese Office Action dated Nov. 4, 2014 from related Chinese Application No. 200180046539.5, together with an English language translation.

(Continued)

*Primary Examiner* — Catherine Voorhees
(74) *Attorney, Agent, or Firm* — Scully, Scott, Murphy & Presser, P.C.

(57) ABSTRACT

A surgical treatment system include a pair of holding members holding a living tissue and a plurality of heater members disposed on at least one of the holding members. The surgical treatment system further includes a resistance pattern which transfer heat to the living tissue, a pair of electrodes disposed at opposite ends of the resistance pattern to generate the heat based on a energy to supply the heat to the resistance pattern, wires each connecting one of the heater members to another heater member and heater member energization line connected to the wire and to a energy source to supply the energy from the energy source to the electrodes via the wire.

5 Claims, 11 Drawing Sheets

(56) References Cited

U.S. PATENT DOCUMENTS

2009/0248002 A1 10/2009 Takashino et al.
2011/0077630 A1* 3/2011 Tanaka et al. .................. 606/29

FOREIGN PATENT DOCUMENTS

| | | |
|---|---|---|
| JP | 2003-275220 A | 9/2003 |
| JP | 2006-158517 A | 6/2006 |
| JP | 2007-037568 A | 2/2007 |
| JP | 2007-037845 A | 2/2007 |
| JP | 2009-247893 A | 10/2009 |

OTHER PUBLICATIONS

International Preliminary Report on Patentability together with the Written Opinion dated Apr. 25, 2013 received in related International Application No. PCT/JP2011/071874.

International Search Report dated Oct. 18, 2011 issued in PCT/JP2011/071874.

* cited by examiner

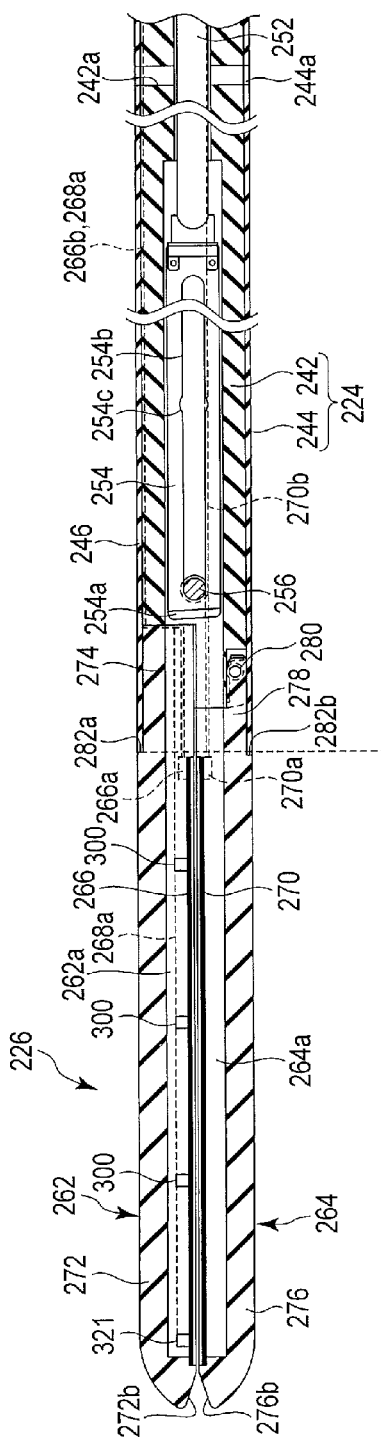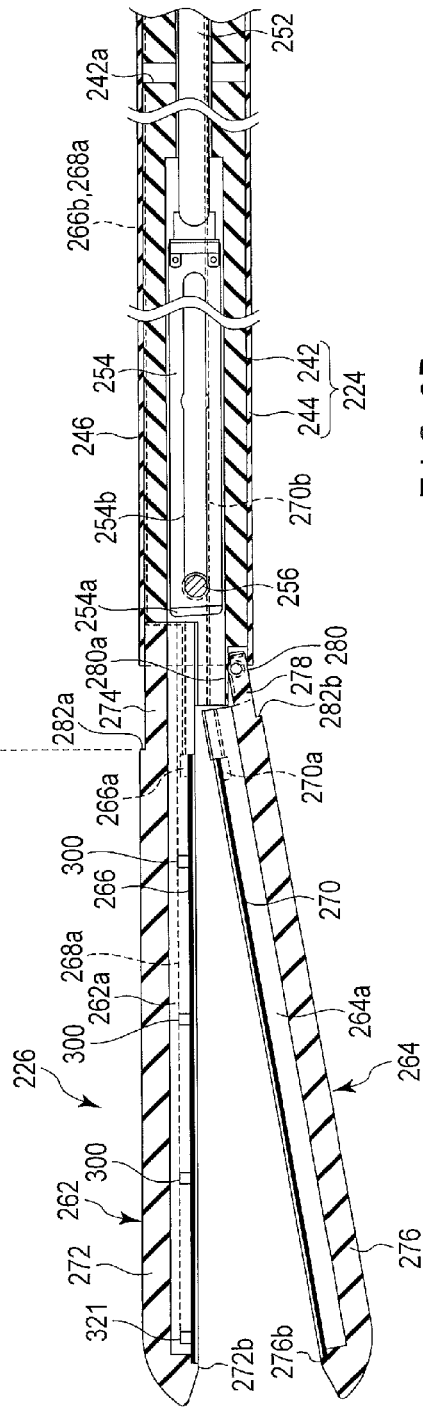
FIG. 2A
FIG. 2B

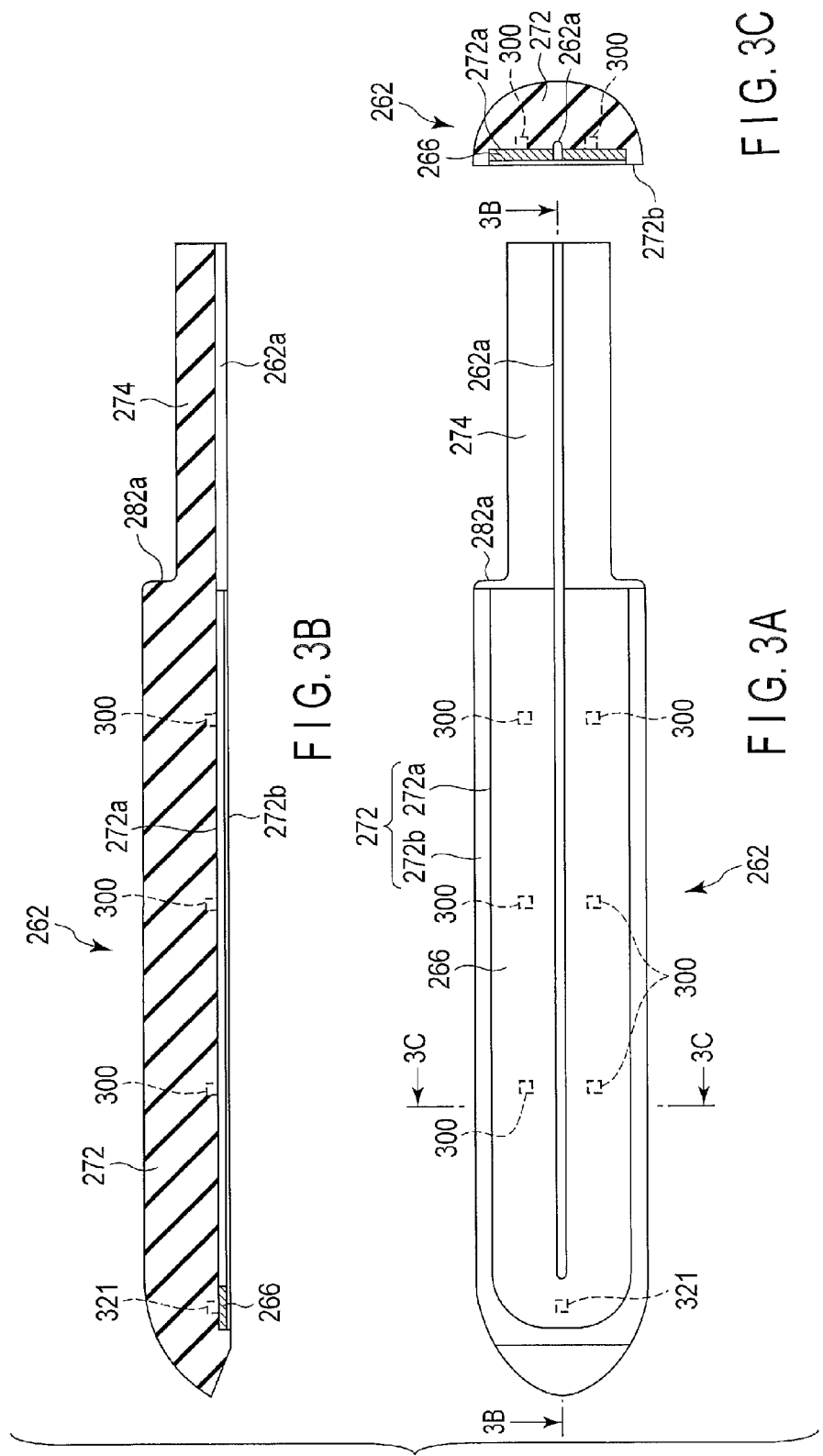

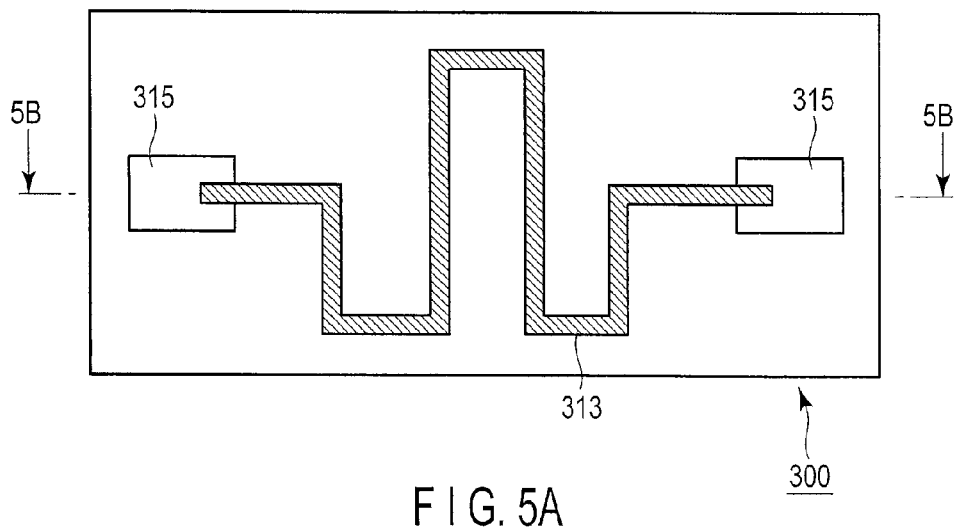
F I G. 5A
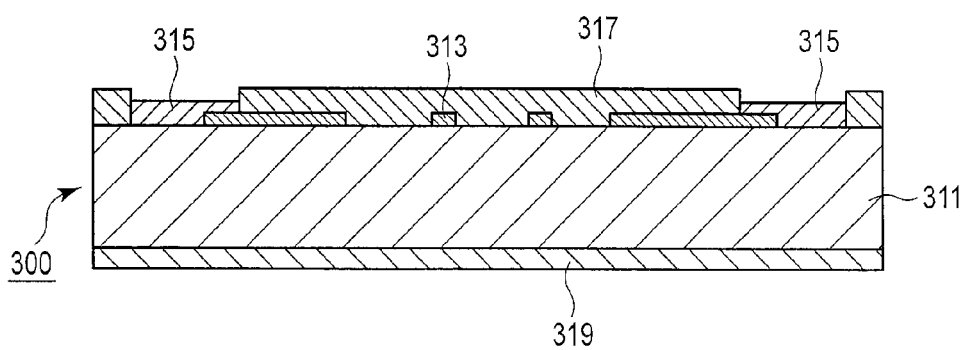
F I G. 5B

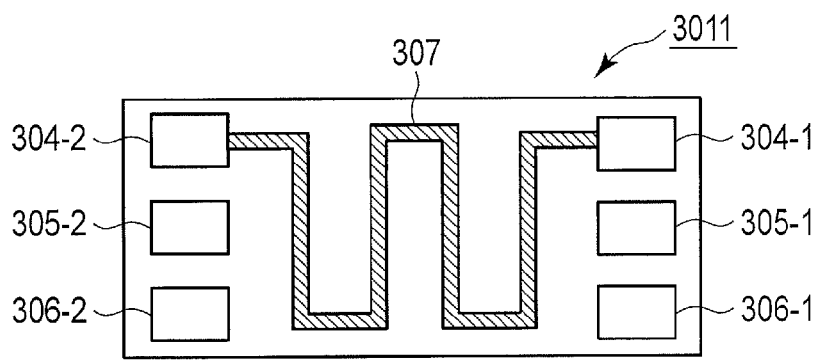
F I G. 11A
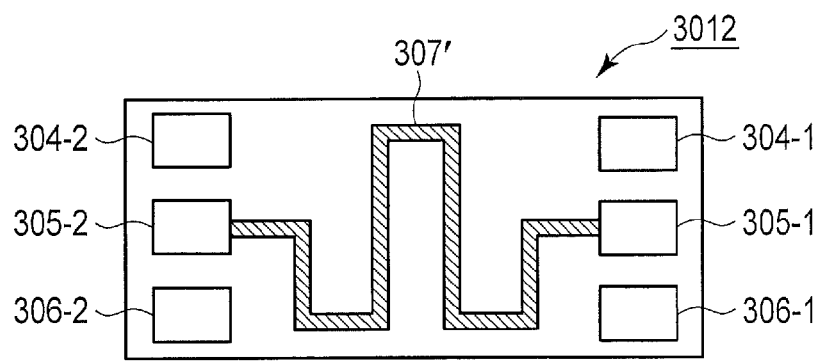
F I G. 11B
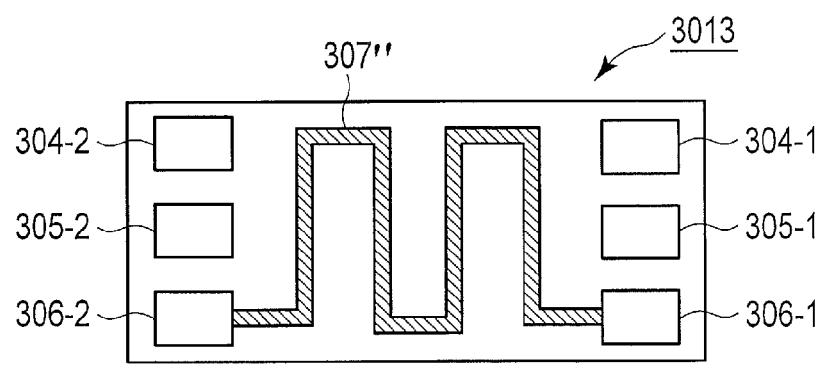
F I G. 11C

SURGICAL TREATMENT SYSTEM

CROSS REFERENCE TO RELATED APPLICATIONS

This application is a Continuation application of PCT Application No. PCT/JP2011/071874, filed Sep. 26, 2011 and based upon and claiming the benefit of priority from prior Japanese Patent Application No. 2010-215961, filed Sep. 27, 2010, the entire contents of all of which are incorporated herein by reference.

BACKGROUND OF THE INVENTION

1. Field of the Invention

The present invention relates to a surgical treatment system which allows living tissue to be treated using energy.

2. Description of the Related Art

For example, Jpn. Pat. Appln. KOKAI Publication No. 2009-247893 discloses a surgical instrument which allows living tissue to be treated using high-frequency energy and thermal energy. To carry out a procedure such as a coagulation procedure or an incision on a living body, the surgical instrument comprises an openable and closable holding section (treatment section) which holds the living tissue. The holding section comprises a pair of holding members. As shown in FIG. 12, a first holding member 2620 comprises a cutter guiding groove 2620a through which a cutter (not shown in the drawings) is guided. Furthermore, the first holding member 2620 comprises a first high-frequency electrode 2660 and a plurality of heater members 3000. FIG. 12 is a schematic diagram showing that the plurality of heater members 3000 are fixed to a back surface of the first high-frequency electrode 2660. A front surface of the first high-frequency electrode 2660 is a contact surface which comes into contact with living tissue. Additionally, the heater members 3000 are discretely disposed on the back surface of the first high-frequency electrode 2660. In this case, the first high-frequency electrode 2660 is insulated from the heater members 3000.

After living tissue is treated by high-frequency energy or thermal energy, the cutter is used to incise a treated site of the living tissue.

The first high-frequency electrode 2660 treats the living tissue with high-frequency energy applied to the first high-frequency electrode 2660.

Heat generated by the heater members 3000 is transferred from the heater members 3000 to the first high-frequency electrode 2660. Thus, the living tissue which is in contact with the first high-frequency electrode 2660 is cauterized. That is, the heater members 3000 treat the living tissue by thermal energy via the first high-frequency electrode 2660.

As described above, the surgical instrument treats the living tissue using high-frequency energy and thermal energy.

The discretely disposed heaters 3000 serve both to control the cost of the heater members 3000 and to keep the temperature of the holding section 2260 uniform.

Furthermore, Jpn. Pat. Appln. KOKAI Publication No. 2007-37845 discloses a surgical instrument which treats living tissue using thermal energy. FIG. 13A and FIG. 13B are diagrams showing a treatment section of the surgical instrument.

A heating treatment section 700 comprises a heating treatment section main body 700a in which heating elements 2100 (2100a, 2100b, and 2100c) are embedded. Each of the heating elements 2100, serving as heating means, is, for example, a thin-plate resistor formed on a ceramic plate. Each of the heating elements 2100 is connected to one end of a lead 2300 (2300a, 2300b, and 2300c) for energization. Furthermore, the other end of the lead 2300 is placed in a connection cable (not shown in the drawings) by being inserted through the connection cable and is then connected to a connection terminal (not shown in the drawings).

This surgical instrument can individually control the amounts of heat generated by the three heating elements 2100, thus making the temperature of the heating treatment section more uniform.

Jpn. Pat. Appln. KOKAI Publication No. 2009-247893 described above fails to disclose a specific method for individually connecting connection cables to the heater members 3000.

Furthermore, Jpn. Pat. Appln. KOKAI Publication No. 2007-37845 described above discloses a method for individually connecting connection cables to the heating elements 2100. Such a connection method requires a large junction area. In particular, the individual control of the amounts of heat generated by the heating elements 2100 involves disposition of a plurality of connection cables. This, however, hinders efforts to reduce the size of the heating treatment section 700, particularly the widthwise dimension thereof. Additionally, the individual connection of the connection cables to the heating elements 2100 increases the cost.

BRIEF SUMMARY OF THE INVENTION

The present invention has been developed in view of these circumstances and object of the present invention is to provide an inexpensive surgical treatment system with a treatment section which is a small-sized even when heater members are connected together.

According to an aspect of embodiments, a surgical treatment system for allowing energy generated by an energy source to act on living tissue to treat the living tissue, the treatment system comprising: a pair of holding members holding the living tissue by moving at least one of the holding members relative to the other holding member; a plurality of heating members disposed on at least one of the holding members and disposed discretely from one another; a heat-generating heat transmission pattern disposed on the respective heating members to transfer heat to the living tissue held by the holding members; a pair of electrodes disposed at opposite ends of the heating heat transfer pattern on each of the heating members to generate the heat based on the energy to supply the heat to the heat-generating heat transmission pattern; wires each electrically connecting one of the heating members to another heating member by wire bonding; and an energization supply section connected to the wire and to the energy source to supply the energy from the energy source to the electrodes on the heating member via the wire.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2(A) is a schematic vertical cross-sectional view showing a shaft of the energy treatment instrument of the surgical treatment system and a first holding member and a second holding member of a holding section which are closed. FIG. 2(B) is a schematic vertical cross-sectional view showing the shaft of the energy treatment instrument and the first holding member and the first holding member and second holding member of the holding section which are open.

FIG. 3(A) is schematic plan view showing the first holding member which is located in proximity to a second holding member of the holding section. FIG. 3 (B) is a schematic vertical cross-sectional view showing the first holding member and taken along line 3B-3B shown in FIG. 3(A). FIG. 3(C) is a schematic horizontal cross-sectional view showing the first holding member and taken along line 3C-3C shown in FIG. 3(A).

FIG. 5A is a top view of the heater member.

FIG. 5B is a cross-sectional view of the heater member taken along line 5B-5B shown in FIG. 5A.

FIG. 11A is a top view of a first heater member according to the third embodiment.

FIG. 11B is a top view of a second heater member according to the third embodiment.

FIG. 11C is a top view of a third heater member according to the third embodiment.

DETAILED DESCRIPTION OF THE INVENTION

Embodiments of the present invention will be described below in detail with reference to the drawings.

A first embodiment will be described with reference to FIG. 1, FIG. 2, FIG. 3, FIG. 4, FIG. 5A, FIG. 5B, FIG. 6A, FIG. 6B, and FIG. 7.

Figure 1:
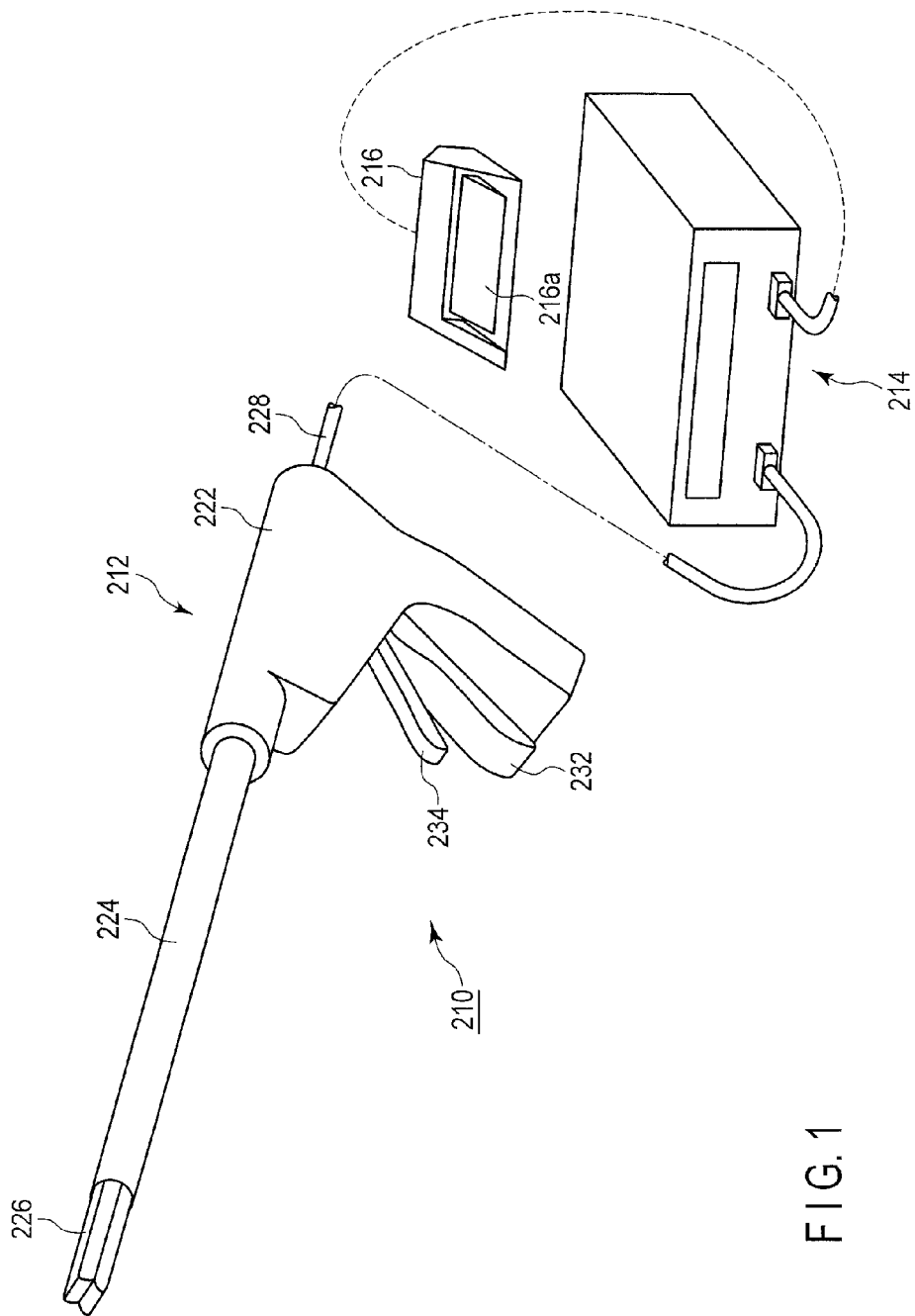
FIG. 1 is a schematic diagram showing a surgical treatment system according to a first embodiment of the present invention.

As shown in FIG. 1, a surgical treatment system 210 comprises an energy treatment instrument 212, an energy source 214, and a foot switch 216. The surgical treatment system 210 allows energy generated by the energy source 214 to act on living tissue via the energy treatment instrument 212 to treat the living tissue.

The energy treatment instrument 212 is a surgical instrument which treats living tissue using high-frequency energy and thermal energy. The energy treatment instrument 212 is a surgical treatment instrument of a linear type which carries out treatment, for example, through the abdominal wall.

The energy treatment instrument 212 comprises a handle 222, a shaft 224, and a holding section 226 which is an openable and closable heating treatment section holding the living tissue to carry out a treatment such as a coagulation treatment or an incision on the living tissue. The handle 222 is connected to the energy source 214 via a cable 228. The energy source 214 is connected to the foot switch (or a hand switch) 216 with a pedal 216a. Thus, when the pedal 216a of the foot switch 216 is operated by a surgeon, the supply of energy from the energy source 214 to the energy treatment instrument 212 is switched on and off.

The handle 212 is shaped so as to be easily gripped by the surgeon. Thus, the handle 222 is, for example, generally L-shaped. The handle 222 comprises a shaft 224 at one end of the handle 222. The handle 222 comprises the cable 228. The cable 228 extends from the other end of the handle 222 disposed coaxially with the shaft 224.

The other end side of the handle 222 forms a gripping section which is gripped by the surgeon. The handle 222 comprises a holding section open and close knob 232 provided on the other end side in juxtaposition. The holding section open and close knob 232 is connected, substantially in the center of the handle 222, to a base end of a sheath 244 (see FIG. 2(A) and FIG. 2(B)) described below, of the shaft 224. When the holding section open and close knob 232 approaches and leaves the other end of the handle 222, the sheath 244 moves along an axial direction of the housing 242.

The handle 222 further comprises a cutter driving knob 234 provided in juxtaposition with the holding section open and close knob 232 to allow a cutter 254 described below to be driven.

As shown in FIG. 2(A) and FIG. 2(B), the shaft 224 comprises a housing 242 and the sheath 244 disposed outside the housing 242. A base end of the housing 242 is fixed to the handle 222 (see FIG. 1). The sheath 244 is slidable along an axial direction of the housing 242 relative to the housing 242.

As shown in FIG. 2(A) and FIG. 2(B), the housing 242 comprises a recess portion 246 formed on an outer side of the housing 242 along the axial direction of the housing 242. The recess portion 246 comprises a first-high-frequency-electrode energization line 266b connected to a first high-frequency electrode 266 described below and a heater member energization line 268a connected to a heating chip, that is, heater members 300 which are heating members. A second-high-frequency-electrode energization line 270b is inserted through the housing 242, and connected to a second high-frequency electrode(output section) 270.

The housing 242 of the shaft 224 comprises a driving rod 252 disposed thereon so as to be movable along the axial direction of the housing 242. The driving rod 252 comprises the cutter 254 provided at a leading end of the driving rod 252, the cutter 254 is an auxiliary treatment instrument and is shaped like, for example, a thin plate. A base end of the driving rod 252 is connected to the cutter driving knob 234. Thus, operation of the cutter driving knob 234 moves the cutter 254 via the driving rod 252.

The cutter 254 comprises an edge 254a at a leading end of the cutter 254. As described above, the base end of the cutter 254 is fixed to the leading end of the driving rod 252. The cutter 254 comprises a slot 254b formed between the leading end and base end of the cutter 254 and shaped like, for example, an ellipse. The slot 254b is disposed along the axial direction of the cutter 254. A movement regulating pin 256 is disposed in the slot 254b. The movement regulating pin 256 extends in a direction orthogonal to the axial direction of the shaft 224. The movement regulating pin 256 is fixed to the housing 242. The cutter 254 moves along the movement regulating pin 256 via the slot 254b. Thus, the cutter 254 moves along the axial direction of the housing 242. At this time, the cutter 254 is disposed in cutter guide grooves (channels or fluid discharge grooves) 262a and 264a in a first holding member 262 and a second holding member 264 described below, respectively.

At least three locations including one end of the slot 254b, the other end of the slot 254b, and the area between the one end and other end of the slot 254b each comprise a locking section 254c which locks the movement regulating pin 256 to control the movement of the cutter 254.

As shown in FIG. 1, FIG. 2(A), and FIG. 2(B), the holding section 226 is disposed at a leading end of the shaft 224. As shown in FIG. 2(A) and FIG. 2(B), the holding section 226 comprises a first holding member (first jaw) 262 and a second holding member (second jaw) 264.

Each of the first holding member 262 and the second holding member 264 preferably generally has insulation properties. The first holding member 262 integrally comprises a first holding section main body (hereinafter mostly referred to as a main body) 272 and a base portion 274 disposed at a base end of the main body 272. The main body 272 and the base portion 274 comprise a cutter guide groove 262a through which the cutter 254 is guided. The main body 272 comprises a first high-frequency electrode 266 and the heater members 300. That is, the first holding member 262 comprises a first high-frequency electrode 266 functioning as an output section or an energy emission section, and the heater members 300.

As shown in FIG. 3(A), FIG. 3(B) and FIG. 3(C) the main body 272 of the first holding member 262 comprises a recess portion 272a and a holding surface 272b including an edge of the recess portion 272a. The first high-frequency electrode 266 is disposed in the recess portion 272a. A front surface of the first high-frequency electrode 266 is different from the holding surface 272b. The holding surface 272b lies in closer proximity, than the front surface of the first high-frequency electrode 266, to a second holding member main body 276 of the second holding member 264 which will be described below and which is located opposite the holding surface 272b is located. That is, the holding surface 272b projects toward the second holding member 264 farther than the front surface of the first high-frequency electrode 266. Furthermore, when the holding section 226 is closed, the holding surface 272b comes into abutting contact with the holding surface 276b of the second holding member main body 276 of the second holding member 264, which is located opposite the holding surface 272b.

As shown in FIG. 2(A) and FIG. 2(B), the first high-frequency electrode 266 is electrically connected to a first electrode connector 266a. The first electrode connector 266a is connected to a cable 228 extended from a handle 222 via the first-high-frequency-electrode energization line 266b.

As shown in FIG. 2(A) and FIG. 2(B), the heater members 300 are connected to the cable 228 extended from the handle 222 via the heater member energization line 268a. The connection between the heater members 300 and the heater member energization line 268a will be described below in detail.

As shown in FIG. 2(A) and FIG. 2(B), the second holding main body of 276 of the second holding member 264 comprises a second high-frequency electrode 270. The second high-frequency electrode 270 is electrically connected to a second electrode connector 270a Furhtermore, the second electrode connector 270a is connected to the cable 228 extended from the handle 222 via a second-high-frequency-electrode energization line 270b.

Figure 4:
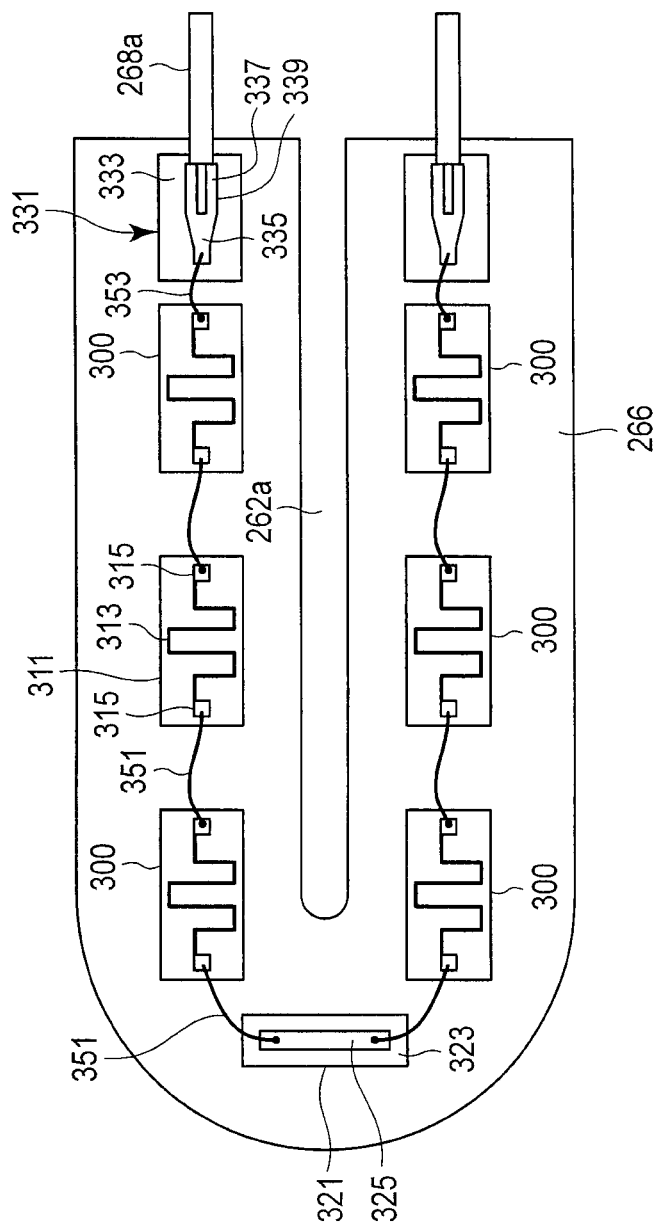
FIG. 4 is a diagram showing how heater members, a relay chip, connection chips, and heater member energization lines are connected together on a first high-frequency electrode.

As shown in FIG. 3(A) and FIG. 4, the first high-frequency electrode 266 is, for example, substantially U-shaped and formed continuously so as to comprise two ends at the base end of the main body 272 of the first holding member 262. Thus, the first high-frequency electrode 266 comprises the cutter guide groove (denoted by reference numeral 262a for convenience) which guides the cutter 254 together with the first holding member 262.

The heater members 300 are discretely disposed from one another on a back surface of the first high-frequency electrode 266. In this case, the first high-frequency electrode 266 and each of the heater members 300 are insulated from each other. When the heater members 300 generate heat, the heat is transferred from the heater members 300 to the first high-frequency electrode 266. Thus, living tissue in contact with the first high-frequency electrode 266 is cauterized.

The main body 272, having insulating properties, preferably covers an outer periphery of the heater members 300 and has heat insulation properties. Such a structure reduces heat loss when the heat generated by the heater members 300 is transferred to the first high-frequency electrode 266.

As shown in FIG. 2(A) and FIG. 2(B), the second holding member 264 integrally comprises the second holding member main body (hereinafter referred to as the main body) 276 and a base portion 278 disposed at the base end of the main body 276. The main body 276 and the base portion 278 comprise the cutter guide groove 264a through which the cutter 254 is guided. The main body 276 comprises the second high-frequency electrode 270. That is, the second holding member 264 comprises the second high-frequency electrode 270 as an output section or an energy emission section.

The second high-frequency electrode 270 is disposed such that the second high-frequency electrode 270 and the first high-frequency electrode 266 shown in FIG. 3(A) are symmetric. Thus, like the first high-frequency electrode 266, the second high-frequency electrode 270 is, for example, substantially U-shaped (the same shape) and formed continuously so as to comprise two ends at the base end of the main body 276 of the second holding member 264. Thus, the second high-frequency electrode 270 comprises a cutter guide groove (denoted by reference numeral 264a for convenience) which guides the cutter 254.

The cutter guide groove 262a in the first holding member 262 and the cutter guide groove 264a in the second holding member 264 are disposed opposite each other and formed along the axial direction of the shaft 224. The two cutter guide grooves 262a and 264a guide one cutter 254.

In the energy treatment instrument 212 shown in FIG. 2(A) and FIG. 2(B), the housing 242 of the shaft 224 comprises a fluid outlet 242a through which a fluid such as a vapor (gas) or a liquid (tissue fluid) described below is emitted. The sheath 244 also comprises a fluid outlet 244a similar to the fluid outlet 242a. The fluid outlets 242a and 244a are formed on the base end side of the shaft 244.

Although not shown in the drawings, a connector ferrule is preferably disposed on an outer peripheral surface of the fluid outlet 244a. In this case, the fluid described below is emitted through the cutter guide grooves 262a and 264a, the fluid outlet 242a in the housing 242, the fluid outlet 244a in the sheath 244, and the connector ferrule. In this case, sucking the inside of the connector ferrule allows the fluid such as the vapor or liquid emitted from living tissue to be easily discharged through the fluid outlets 242a and 244a.

The fluid outlets 242a and 244a are preferably disposed in the shaft 224 but are also preferably disposed in the handle 222 instead of the shaft 224.

The base portion 274 of the first holding member 262 is fixed to a leading end of the housing 242. The base portion 278 of the second holding member 264 is pivotally supported at the leading end of the housing 242 by a support pin 280. The support pin 280 is disposed in a direction orthogonal to the axial direction of the shaft 224. The second holding member 264 can be opened and closed with respect to the first holding member 262 by being pivotally moved around the axis of the support pin 280. The first holding member 262 can be opened and closed with respect to the second holding member 264. That is, at least one of the first holding member 262 and the second holding member 264 moves relative to the other to hold (grip) living tissue. The second holding member 264 is biased by an elastic member 280a, for example, a sheet spring, so as to be opened with respect to the first holding member 262.

In the first holding member 262, an outer surface of the main body 272 and an outer surface of the base portion 274 are formed like smooth curved surfaces. Similarly, in the second holding member 264, an outer surface of the main body 276 and an outer surface of the base portion 278 are formed like smooth curved surfaces. With the second holding member 264 closed with respect to the first holding member 262 as shown in FIG. 2(A), cross sections of the main bodies 272 and 276 are shaped substantially like circles or ellipses. With the second holding member 264 closed with respect to the first holding member 262, the holding surface 272b of the main body 272 and the holding surface 276b of the main body 276 are located opposite each other. The base potions 274 and 278 are formed like cylinders. In this condition, the diameter of the base ends of the main bodies 272 and 276 is formed to be larger than the diameter of the base portions 274 and 278. A step 282a is formed between the main body 272 and the base portion 274. A step 282b is formed between the main body 276 and the base portion 278.

With the second holding member 264 closed with respect to the first holding member 262 as shown in FIG. 2(A), a substantially circular or substantially elliptic outer peripheral surface formed by the base portions 274 and 278 is formed to be substantially flush with or slightly larger than an outer peripheral surface of the leading end of the housing 242. Thus, when the sheath 244 slides toward the leading end of the housing 242 along the axial direction of the housing 242 with respect to the housing 242, a leading end of the sheath 244 can cover the base portions 274 and 278. In this condition, as shown in FIG. 2(A), the first holding member 262 and the second holding member 264 are closed against the bias force of the elastic member 280a. Furthermore, with the leading end of the sheath 244 covering the base portions 274 and 278, when the sheath 244 slides toward the base end of the housing 242 along the axial direction of the housing 242, then as shown in FIG. 2B, the base portions 274 and 278 are exposed, and the bias force of the elastic member 280a causes the second holding member 264 to be opened with respect to the first holding member 262.

Furthermore, according to the present embodiment, as shown in FIG. 4, the distance between the base ends of the first high-frequency electrode 266 is formed, for example, to be equal to the width of the cutter guide groove 262a in the first holding member 262 in the direction of width of the first high-frequency electrode 266 which is orthogonal to a longitudinal direction of the first high-frequency electrode 266. Similarly, the distance between the base ends of the second high-frequency electrode 270 is formed, for example, to be equal to the width of the cutter guide groove 264a in the second holding member 264. The distance between the base ends of the first high-frequency electrode 266 and the distance between the base ends of the second high-frequency electrode 270 can be set as appropriate. Additionally, the first high-frequency electrode 266 may be disposed away from an edge of the cutter guide groove 262a. The second high-frequency electrode 270 may be disposed away from an edge of the cutter guide groove 264a.

Now, with reference to FIG. 4, FIG. 5A, FIG. 5B, FIG. 6A, FIG. 6B, and FIG. 7, the following will be described: the heater member 300, a relay chip 321, connection chips 331, the first high-frequency electrode 266, and connections among the heater member 300, the chips 321 and 331, and the first high-frequency electrode 266.

With reference to FIG. 5A and FIG. 5B, the heater member 300 will be described.

The heater member 300 is a heat generation member which generates heat. The heater member 300 comprises a substrate 311 formed of alumina, a heater (heating) resistance pattern 313 which is a thin Pt film formed on a front surface of the substrate 311, a pair of rectangular electrodes 315 disposed on the front surface of the substrate 311 and connected to one end and the other end, respectively, of the resistance pattern 313, an insulating polyimide film 317 covering a part of the front surface of the substrate 311 which excludes the electrodes 315 and which includes the resistance pattern 313, and a backside electrode 319 formed all over a back surface of the substrate 311.

The resistance pattern 313 is a heat-generating heat transmission pattern which transfers heat to living tissue held (gripped) by the first holding member 262 and the second holding member 264 in order to treat the living tissue.

The electrode 315 generates heat based on energy supplied by the energy source 214 via the heater member energization line 268a and wires 351 and 353 to supply the heat to the resistance pattern 313.

The electrode 315 and the backside electrode 319 are multilayer films formed of, for example, Ti, Cu, Ni, and Au. The thickness of each of the films is adjusted so as to enable the film to be connected or joined so as to achieve a stable strength in connection with wire bonding or soldering.

A plurality of heater members 300 are disposed along the longitudinal direction of the first high-frequency electrode 266. The heater members 300 are disposed in series. For the adjacent heater members 300, a first heater member 300 and a second heater member 300 are connected together by the wire 351 for wire bonding. That is, the wire 351 electrically connects the first heater member 300 and the second heater member 300 together by wire bonding. More specifically, the wire 351 electrically connects one of the electrodes 315 on the first heater member 300 and the other of the electrodes 315 on the second heater member 300 together by wire bonding.

Now, the first high-frequency electrode 266 will be described.

The first high-frequency electrode 266 is, for example, thin copper plate.

The front surface of the first high-frequency electrode 266 comes into contact with living tissue.

Back surfaces (backside electrodes 319) of six heaters 300 are soldered to the back surface of the first high-frequency electrode 266. Furthermore, as shown in FIG. 4, the first high-frequency electrode 266 comprises the relay chip 321. The relay chip 321 is soldered to a bottom portion of the back surface of the U-shaped first high-frequency electrode 266. The relay chip 321 is disposed to electrically connect one heater member 300 and another heater member 300 which are disposed on the bottom side. The relay chip 321 is disposed because a distance between the heater members 300 disposed in the direction of width of the first high-frequency electrode 266 is longer than the distance between the heater members 300 disposed in series along the longitudinal direction of the first high-frequency electrode 266. According to the present embodiment, the distance between the heater members 300 in the longitudinal direction of the first high-frequency electrode 266 is, for example, 5 mm.

Furthermore, the first high-frequency electrode 266 comprises the connection chips 331 at the opposite ends of the back surface of the first high-frequency electrode 266. Each of the connection chips 331 is soldered to the back surface. One of the connection chips 331 connects one heater member 300 and the heater member energization line 268a together. The other connection chip 331 connects another heater member 300 and the heater member energization line 268a together. Each of the connection chips 331 is connected to the heater member 300 by the wire 353 for wire bonding. The heater member energization line 268a is an energization supply section which connects to the wire 353 and the energy source 214 to supply the energy from the energy source 214 to the electrodes 315 of the heater members 300 via the wires 351 and 353.

Figure 6A:
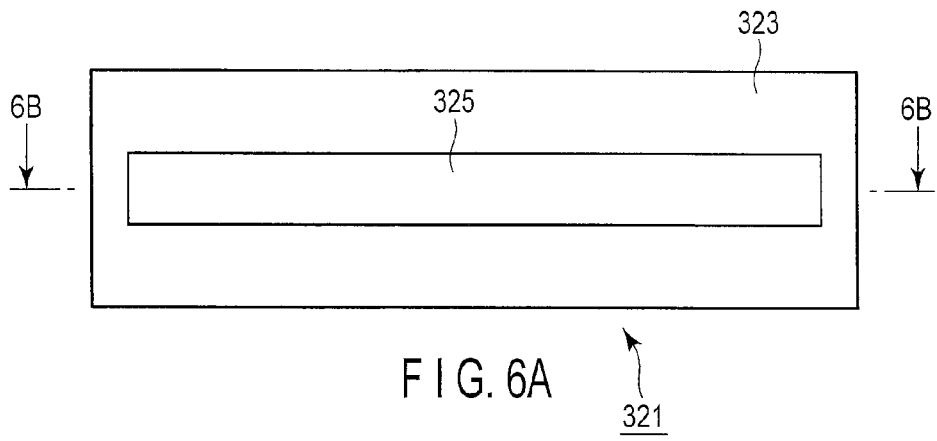
FIG. 6A is a top view of the relay chip.
Figure 6B:
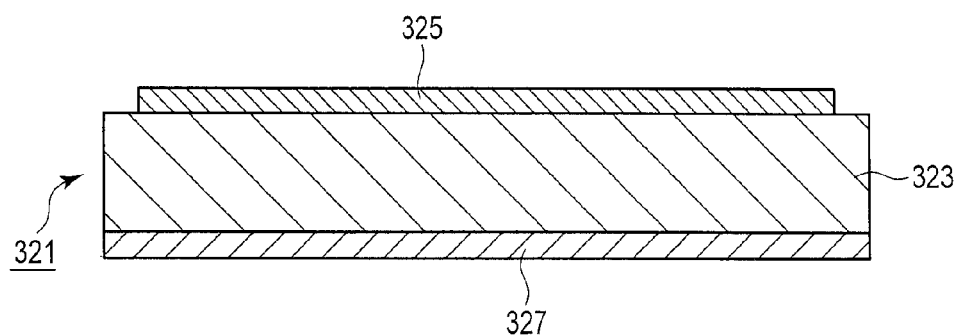
FIG. 6B is a cross-sectional view of the relay chip taken along line 6B-6B shown in FIG. 6A.

Now, with reference to FIG. 6A and FIG. 6B, the relay chip 321 will be described.

The relay chip 321 comprises a substrate 323 formed of alumina, a rectangular electrode 325 disposed on a front surface of the substrate 323 and connected to the electrodes 315 by the wires 351 for wire bonding as shown in FIG. 4, and a backside electrode 327 formed all over a back surface of the substrate 323.

The relay chip 321 is soldered to the back surface of the first high-frequency electrode 266 via the backside electrode 327.

Figure 7:
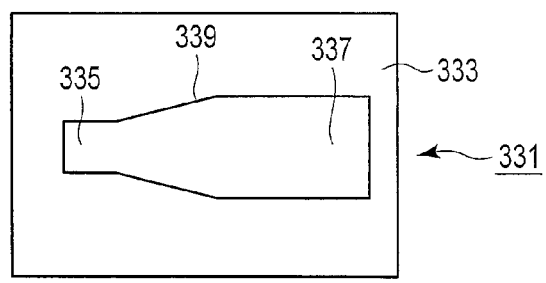
FIG. 7 is a top view of the connection chip.

Now, with reference to FIG. 7, the connection chip 331 will be described.

The connection chip 331 is configured similarly to the relay chip 321. That is, the connection chip 331 comprises a substrate 333 formed of alumina, a rectangular electrode 339 disposed on a front surface of the substrate, and a backside electrode formed all over a back surface of the substrate.

The connection chip 331 is soldered to the back surface of the first high-frequency electrode 266 via the backside electrode.

The electrode 339 has a leading end 335 and a base end 337. The electrode 339 is connected to the electrode 315 at the leading end 335 by the wire 353 for wire bonding and to the heater member energization line 268a at the base end 337 by soldering.

According to the present embodiment, the heater members 300, the relay chip 321, and the connection chips 331 are connected together in series by the wires 351 and 353 for wire bonding and are disposed along the substantial U shape of the first high-frequency electrode 266.

Now, a method for operation of the heater member 300 according to the present embodiment will be described.

A display section (not shown in the drawings) of the energy source 214 is pre-operated by an operator to set output conditions for the treatment system 210. Specifically, for example, the following are set: set electric power Pset [W] for high-frequency energy output, set temperature Tset [° C.] for thermal energy output, thresholds Z1 and Z2 for the impedance Z of living tissue, and the like.

As shown in FIG. 2(A), with the second holding member 264 closed with respect to the first holding member 262, for example, the holding section 226 and shaft 224 of the energy treatment instrument 212 are inserted into the abdominal cavity through the abdominal wall. The holding section 226 is located opposite living tissue to be treated.

The holding section open and close knob 232 of the handle 222 is operated to allow the first holding member 262 and the second holding member 264 to hold the living tissue to be treated. Thus, the sheath 244 slides toward the base end side of the shaft 224 with respect to the housing 242. Then, the bias force of the elastic member 280a allows the second holding member 264 to be opened with respect to the first holding member 262.

The living tissue is placed between the first high-frequency electrode 266 of the first holding member 262 and the second high-frequency electrode 270 of the second holding member 264. In this condition, the holding section open and close knob 232 of the handle 222 is operated. At this time, the sheath 244 slides toward the leading end side of the shaft 224 with respect to the housing 242. Then, the sheath 244 covers the base portions 274 and 278 against the bias force of the elastic member 280a. This allows closing of the main body 272 of the first holding member 262 formed integrally with the base portion 274 and the main body 276 of the second holding member 264 formed integrally with the base portion 278. That is, the second holding member 264 is closed with respect to the first holding member 262. In this manner, the first holding member 262 and the second holding member 264 grip the living tissue.

At this time, the first high-frequency electrode 266 disposed on the first holding member 262 and the second high-frequency electrode 270 disposed on the second holding member 264 are in contact with the living tissue. At this time, the holding surface 272b of the first holding member 262 and the holding surface 276b of the second holding member 264 are in tight contact with a peripheral tissue of the living tissue.

With the first holding member 262 and the second holding member 264 gripping the living tissue, the foot switch 216 is operated. Switching the foot switch 216 on allows energy to be fed from the energy source 214 to the first high-frequency electrode 266 and the second high-frequency electrode 270 via the cable 228. At this time, the first high-frequency electrode 266 and the second high-frequency electrode 270 are supplied with the preset set electric power Pset [W], for example, electric power of about 20 [W] to 80 [W].

Thus, a high-frequency current flows through the living tissue gripped by the first holding member 262 and the second holding member 264. The high-frequency current heats the living tissue to start cauterizing the living tissue (degenerating the tissue).

Cauterizing the living tissue as described above allows a fluid (for example, a liquid (blood) and/or a gas (steam)) to be emitted from the living tissue. At this time, the holding surfaces 272b and 276b are in tighter contact with the living tissue than the first high-frequency electrode 266 and the second high-frequency electrode 270. Thus, the holding surfaces 272b and 276b function as a barrier section (dam) which restrains the fluid from escaping to the outside of the first holding member 262 and the second holding member 264. Thus, the fluid flows into the cutter guide groves 262a and 264a and is, for example, sucked from the first holding member 262 and the second holding member 264 toward the shaft 224. While being emitted from the living tissue, the fluid continues to flow into the cutter guide grooves 262a and 264a. This prevents possible thermal spread caused by the fluid emitted from the living tissue with the temperature thereof remaining higher, thus preventing sites not to be treated from being affected by the fluid.

Then, the energy source 214 supplies electric power to the heater members 300 so that the temperature of the heater members 300 reaches the preset temperature Tset [° C.], for example, 100 [° C.] to 300 [° C.]. At this time, electric power is fed from the energy source 214 to the heater members 300 through the cable 228, the heater member energization line 268a, the connection chips 331, and the wires 353 for wire bonding. The heater members 300 are connected together in series by the relay chip 321 and the wires 351 for wire bonding. Thus, electric power is fed from the heater member energization line 268a to the heater member 300 in order. Electric Power is fed from the heater member 300 disposed on the base end (heater member energization line 268a) side of the first high-frequency electrode 266 to the heater member 300 disposed on the leading end (relay chip 321) side of the first high-frequency electrode 266.

The electrode 315 generates heat based on electric power supplied through the heater member energization line 268a and the wires 351 and 353 and feeds heat to the resistance pattern 313. The resistance pattern 313 transfers heat to the first high-frequency electrode 266 owing to heat transfer. The heat solidifies the living tissue in tight contact with the first high-frequency electrode 266 so that the solidification proceeds from the surface of the living tissue toward the inside thereof.

Then, the energy source 214 stops outputting high-frequency energy and thermal energy. This completes the treatment of the living tissue using the treatment system 210.

Thus, the present embodiment allows the heater members 300, which are heating members, to be connected together in series by the wires 351 and 353 for wire bonding. The present embodiment also enables the size of the holding section 226, which is a heat-generating treatment section, to be reduced particularly in the direction of the width.

Furthermore, according to the present embodiment, the heater members 300 are connected together in series by the wires 351 and 353 for wire bonding, thus eliminating the need to connect heater member energization lines 268a which is connection cables individually to the heater members 300. As a result, the present embodiment reduces costs. Thus, the present embodiment can provide an inexpensive surgical instrument with the holding section 226 which is a small-sized treatment section.

Additionally, according to the present embodiment, even though the heater members 300 are connected together in series and discretely disposed along the substantial U shape of the first high-frequency electrode 266, the distance between the heater members 300 can be reduced by the relay chip 321 and the wires 351 and 353 for wire bonding. Thus, the wires can be stably disposed.

In addition, according to the present embodiment, the heater members 300, the relay chip 321, and the connection chips 331 can be formed using the substrates 311 and 323 formed of alumina, which can be soldered to the back surface of the first high-frequency electrode 266. The heater members 300, the relay chip 321, and the connection chips 331 can be connected together in series by the wires 351 and 353 for wire bonding.

A die bonder for use in general fabrication of semiconductor devices can be utilized to solder ceramic chips such as the heater members 300, the relay chip 321, and the connection chips 331. Furthermore, a wire bonder for use in general fabrication of semiconductor devices can be utilized for wire bonding for connection of the heater members 300. These fabrications of semiconductor devices are very productive. Thus, the present embodiment inexpensively enables the heater members 300, the relay chip 321, and the connection chips 331 to be soldered to (mounted on) the back surface of the first high-frequency electrode 266, and allows the heater members 300 to be connected together by the wires 351 for wire bonding.

Furthermore, the present embodiment enables the distance between the heater members 300 to be set to, for example, 5 mm, that is, allows the heater members 300 to be disposed in close proximity to each other.

Now, a second embodiment according to the present invention will be described with reference to FIG. 8 and FIG. 9. The same components of the second embodiment as the corresponding components of the first embodiment are denoted by the same reference numerals as those in the first embodiment. Description of these components is omitted.

According to the present embodiment, for example, four heater members 300 are disposed. As shown in FIG. 9, each heater member 300 further comprises an electrode 315a which is provided on the front surface of the substrate 311 with the electrode 315 disposed thereon and which is electrically insulated from the electrode 315. An insulating polyimide film according to the present embodiment covers a part of the front surface of the substrate 311 which does not include the portions of the electrode 315 and the electrode 315a but includes the portion of the resistance pattern 313.

Figure 8:
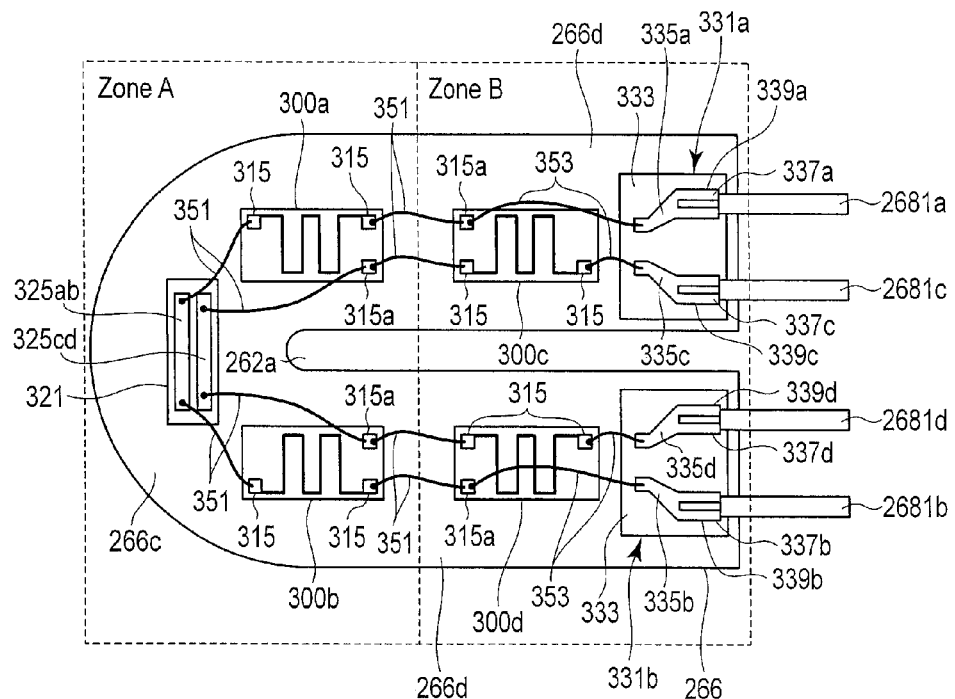
FIG. 8 is a diagram showing how the heater members, the relay chip, the connection chips, and the heater member energization lines are connected together on the first high-frequency electrode according to a second embodiment.
Figure 9:
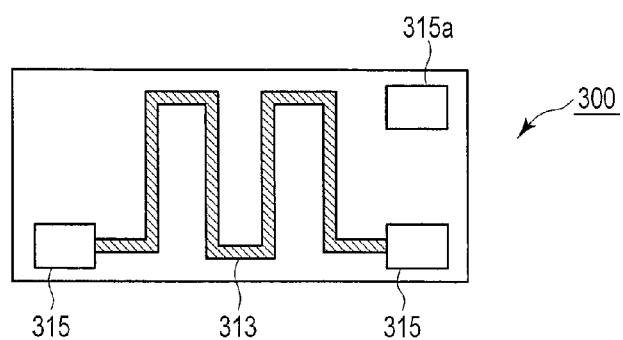
FIG. 9 is a top view of the heater member according to the second embodiment.

Furthermore, according to the present embodiment, as shown in FIG. 8, the heater members 300 on a leading end 266c side of the first high-frequency electrode 266 are controlled separately from and independently of the heater members 300 on a base end 266d side of the first high-frequency electrode 266. Thus, the first high-frequency electrode 266 comprises a zone A on the leading end 266c side and a zone B on the base end 266d side. Zone A comprises a heater member 300a and a heater member 300b. Zone B comprises a heater member 300c and a heater member 300d. The heater members 300 are thus divided into a plurality of groups.

First, the zone A side will be described.

For the heater member 300a and heater member 300b in zone A, heater member energization lines 2681a and 2681b are disposed, and a connection chip 331a comprises an electrode 339a. Moreover, a connection chip 331b comprises an electrode 339b, and the relay chip 321 comprises an electrode 325ab.

The heater members 300a and 300b, the heater member energization lines 2681a and 2681b, the electrodes 339a and 339b, and the electrode 325ab are disposed so as to be electrically connected together in series.

The electrodes 339a and 339b have the same configuration as the configuration of the electrode 339. The electrode 325ab has the same configuration as the configuration of the electrode 325.

Now, the series connection will be described.

The heater member energization line 2681a is connected to a base end 337a of the electrode 339a by soldering. A leading end 335a of the electrode 339a is connected to the electrode 315a of the heater member 300c by the wire 353 for wire bonding. The electrode 315a is connected to one of the electrodes 315 of the heater member 300a by the wire 351 for wire bonding. Furthermore, the other electrode 315 is connected, by the wire 351 for wire bonding, to one end of the electrode 325ab disposed on the relay chip 321.

Additionally, the heater member energization line 2681b is connected to a base end 337b of the electrode 339b by soldering. A leading end 335b of the electrode 339a is connected to the electrode 315a of the heater member 300d by the wire 353 for wire bonding. The electrode 315a is connected to one of the electrodes 315 of the heater member 300b by the wire 351 for wire bonding. Furthermore, the other electrode 315 is connected, by the wire 351 for wire bonding, to the other end of the electrode 325ab disposed on the relay chip 321.

The heater member 300a and the heater member 300b are disposed symmetrically with respect to the cutter guide groove 262a. In this case, for example, the electrodes 315a of the heater member 300a and the heater member 300b are disposed closer to the cutter guide groove 262a than the electrodes 315 of the heater member 300a and the heater member 300b.

Then, the zone B side will be described.

For the heater member 300c and heater member 300d in zone B, heater member energization lines 2681c and 2681d are disposed, and the connection chip 331a comprises an electrode 339c. Moreover, the connection chip 331b comprises an electrode 339d, and the relay chip 321 comprises an electrode 325cd.

The heater members 300c and 300d, the heater member energization lines 2681c and 2681d, the electrodes 339c and 339d, and the electrode 325cd are disposed so as to be electrically connected together in series.

The electrodes 339c and 339d have the same configuration as the configuration of the electrode 339. The electrode 325cd has the same configuration as the configuration of the electrode 325.

Now, the series connection will be described.

The heater member energization line 2681c is connected to a base end 337c of the electrode 339c by soldering. A leading end 335c of the electrode 339c is connected to one of the electrodes 315 of the heater member 300c by the wire 353 for wire bonding. The other electrode 315 of the heater member 300c is connected to the electrodes 315a of the heater member 300a by the wire 351 for wire bonding. The electrode 315a is connected, by the wire 351 for wire bonding, to one end of the electrode 325cd disposed on the relay chip 321.

Additionally, the heater member energization line 2681d is connected to a base end 337d of the electrode 339d by soldering. A leading end 335d of the electrode 339a is connected to the one of the electrodes 315 of the heater member 300d by the wire 353 for wire bonding. The other electrode 315 of the heater member 300d is connected to the electrode 315a of the heater member 300b by the wire 351 for wire bonding. The electrode 315a is connected, by the wire 351 for wire bonding, to the other end of the electrode 325cd disposed on the relay chip 321.

The heater member 300c and the heater member 300d are disposed symmetrically with respect to the cutter guide groove 262a. In this case, for example, the electrodes 315 of the heater member 300c and the heater member 300d are disposed closer to the cutter guide groove 262a than the electrodes 315a of the heater member 300c and the heater member 300d.

Thus, as shown in FIG. 8, for example, the wire 351 electrically connects, by wire bonding, one of the electrodes 315 disposed on each of the heater members 300a and 300b in zone A to the electrode 315a disposed on the corresponding one of the heater members 300c and 300d in zone B. The wire 351 electrically connects, by wire bonding, the electrode 315a disposed on each of the heater members 300a and 300b in zone A to one of the electrodes 315 of the corresponding one of the heater members 300c and 300d in zone B.

The wires 353 electrically connect the electrodes 315a disposed on the heater members 300c and 300d in zone B and the other electrodes 315 disposed on the heater members 300c and 300d in zone B to heater member energization lines 2681a, 2681b, 2681c, and 2681d, respectively, by wire bonding via the connection chips 331a and 331b.

Furthermore, the heater member energization lines 2681a, 2681b, 2681c, and 2681d supply energy, via the wires 351 and 353, to the electrodes 315 disposed on the heater members 300 in zone A and zone B. Thus, energy is supplied separately to each group of the heater members 300.

A method for operation of the heater member 300 according to the present embodiment is substantially similar to the method for operation of the heater member 300 according to the first embodiment. Detailed description of the method is omitted.

According to the present embodiment, the destination of electric power is switched between zone A and zone B based on the amount by which a pedal 216a of the foot switch 216 is depressed or by a switch (not shown in the drawings) disposed in the energy source 214. Thus, the group of heater members 300 in zone A and the group of heater members 300 in zone B are controlled separately from and independently of each other so that the two groups of heater members 300 can treat the living tissue independently of each other.

Hence, the present embodiment can exert effects similar to the effects of the first embodiment.

Furthermore, the present embodiment can control the group of heater members 300 on the leading end 266c side (zone A) of the first high-frequency electrode 266 and the group of heater members 300 on the base end 266d side (zone B) of the first high-frequency electrode 266 independently of each other so that the two zones can treat the living tissue independently of each other.

Additionally, according to the present embodiment, even if the heater members 300 are not adjacent to each other along the axial direction of the first high-frequency electrode 266, the electrode 315a enables series connection of the heater members 300 in the direction orthogonal to the axial direction of the first high-frequency electrode 266, that is, in the direction of width of the holding section 226.

Furthermore, according to the present embodiment, the electrodes 315a of the heater members 300a and 300b need not connect the other electrode 315 of each of the heater members 300c and 300d to the electrode 325cd along the axial direction of the first high-frequency electrode 266 by the wires 351 for wire bonding. In addition, according to the present embodiment, the electrodes 315a of the heater members 300c and 300d need not connect each of the leading ends 335a and 335b of the electrodes 339a and 339b to one of the electrodes 315 of the corresponding one of the heater members 300a and 300b by the wires 353 for wire bonding. Thus, the present embodiment can prevent a situation in which the electrodes 315a are used as relay sections for the connections by the wires 351 and 353, excessively increasing loop length (the length of the wires 351 and 353 for wire bonding) to make the shape of the wires 351 and 353 unstable. Consequently, the present embodiment can improve the yield of the wires 351 and 353.

Additionally, the present embodiment can thus reduce the length of the wires 351 and 353 to suppress an increase in the height of the wires 351 and 353 (which corresponds to a direction perpendicular to a plane (first high-frequency electrode 266) with the wires 351 and 353 installed thereon). The present embodiment can provide the energy treatment instrument 212 which is an inexpensive surgical instrument with the holding section 226 which is a small-sized treatment section.

Now, a third embodiment according to the present invention will be described with reference to FIG. 10, FIG. 11A, FIG. 11B, and FIG. 11C. The same components of the third embodiment as the corresponding components of the first and second embodiments are denoted by the same reference numerals as those in the first and second embodiments. Description of these components is omitted.

Figure 10:
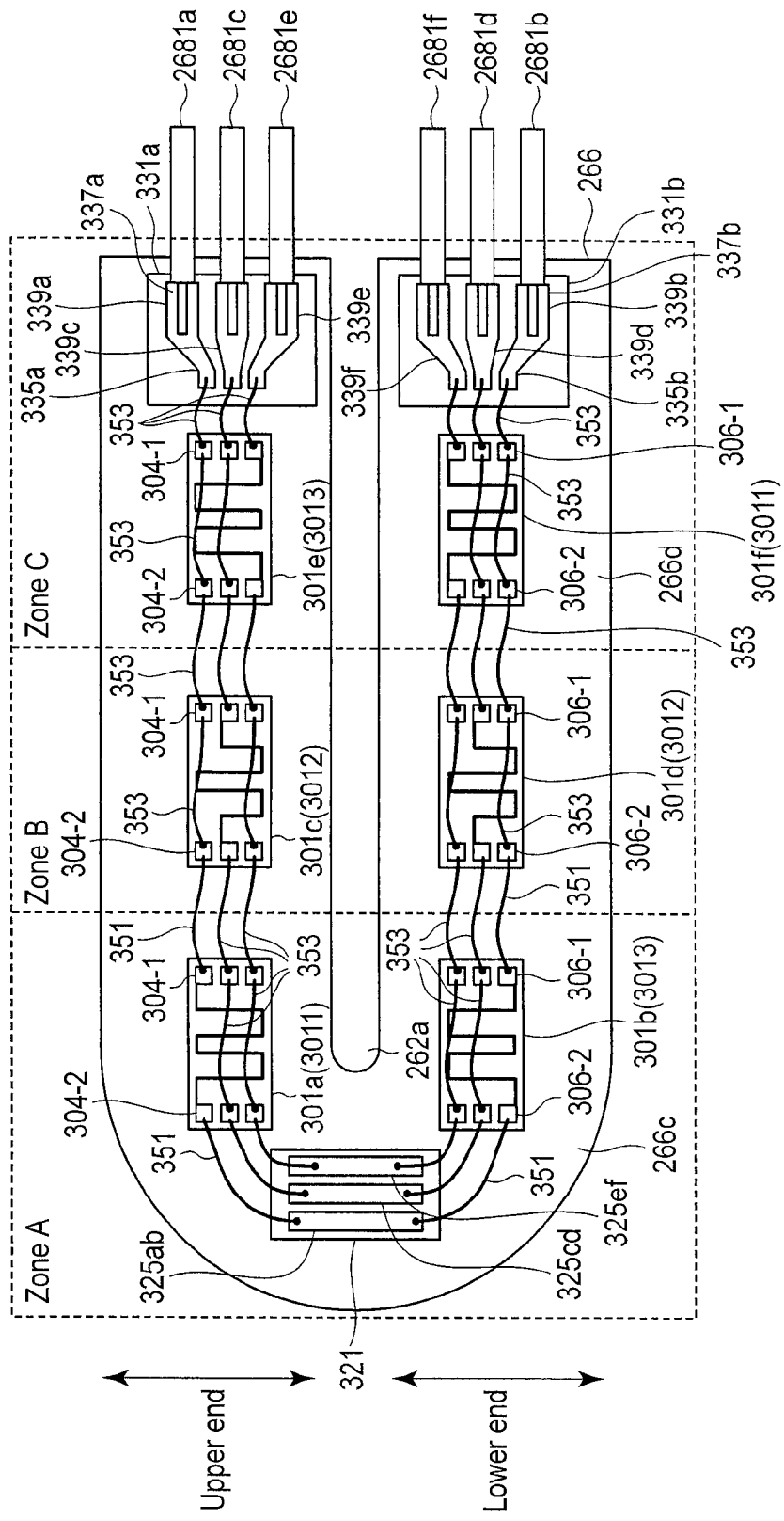
FIG. 10 is a diagram showing how the heater members, the relay chip, the connection chips, and the heater member energization lines are connected together on the first high-frequency electrode according to a third embodiment.
Figure 12:
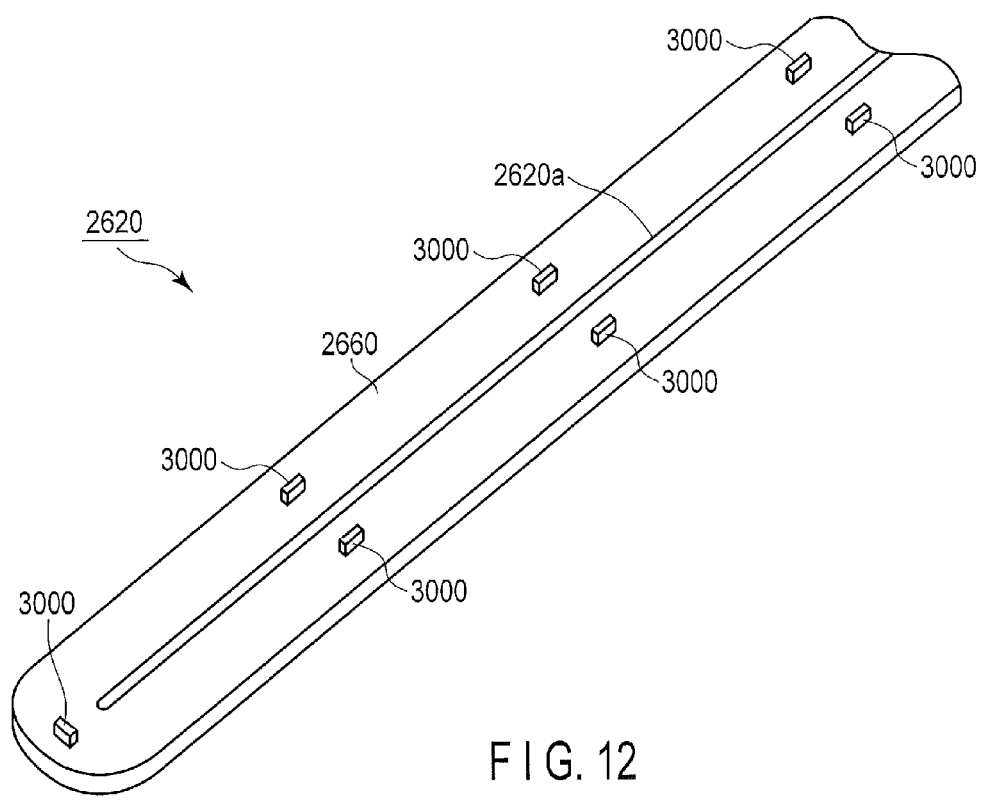
FIG. 12 is a perspective view of a general first high-frequency electrode with heater members disposed thereon.
Figure 13A:
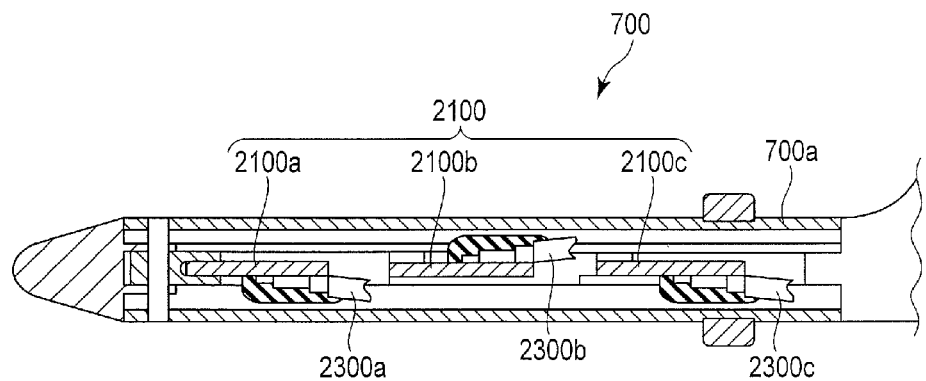
FIG. 13A is a top-surface cross-sectional view of the general heating treatment section as seen from a top surface thereof in the vertical direction.
Figure 13B:
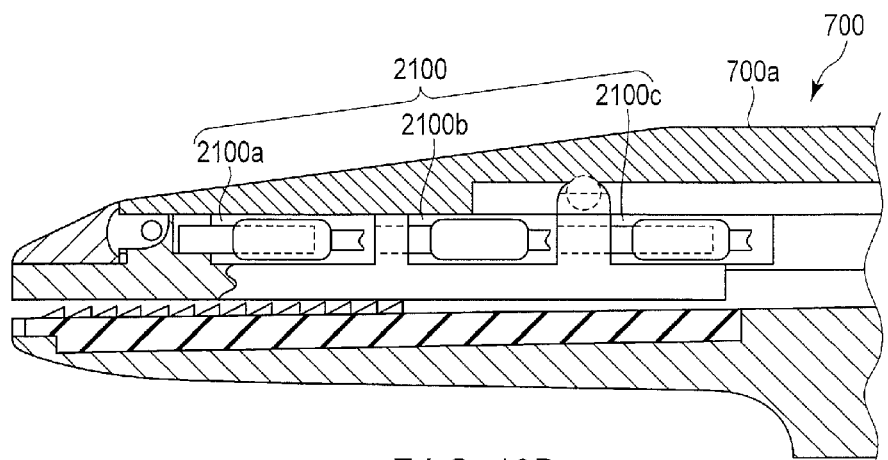
FIG. 13B is a top-surface cross-sectional view of the general heating treatment section as seen from a side surface thereof in the horizontal direction.

As shown in FIG. 10, the first high-frequency electrode 266 comprises a zone A on the leading end 266c side, a zone B disposed between the leading end 266c side and the base end 266d side, and a zone C on the base end 266d side. The first high-frequency electrode 266 controls the group of heater members 300 on the leading end 266c side of the first high-frequency electrode 266 (zone A), the group of heater members 230 between the leading end 266c side and base end 266d side of the first high-frequency electrode 266 (zone B), and the group of heater members on the base end 266d side of the first high-frequency electrode 266 (zone C) separately from and independently of one another.

Now, as shown in FIG. 11A, FIG. 11B, and FIG. 11C, the heater member 300 according to the present embodiment will be described.

According to the present embodiment, six heater members 300 are disposed. Furthermore, the present embodiment uses three types of heater members 3011, 3012, and 3013 with different layouts. However, the heater member 3013 is configured to have a different layout for convenience of description. In actuality, the heater member 3013 is obtained by rotating the heater member 3011 through 180 degrees.

As shown in FIG. 11A, the heater member 3011 comprises three pairs of electrodes at the opposite ends of the heater member 3011. These pairs of electrodes are hereinafter referred to as upper-stage electrodes 304, middle-stage electrodes 305, and lower-stage electrodes 306. Furthermore, for convenience of description, the right electrodes in FIG. 11A are denoted by a suffix -1, whereas the left electrodes in FIG. 11A are denoted by the suffix -2. This configuration also applies to the heater members 3012 and 3013 as shown in FIG. 11B and FIG. 11C.

As shown in FIG. 11A, the heater member 3011 comprises a heater (heating) resistance pattern 307 formed in the entire area of the heater member 3011 except for the areas of the opposite ends of the heater member 3011. The opposite ends of the resistance pattern 307 are connected to the upper-stage electrodes 304. A total of four electrodes including the middle-stage electrodes 305 and the lower-stage electrodes 306 are electrically insulated from one another. Furthermore, the upper-stage electrodes 304 are electrically insulated from the middle-stage electrodes 305 and the lower-stage electrodes 306. Thus, on a front surface of the substrate with the upper-stage electrodes 304 disposed thereon, the heater member 3011 further comprises the middle-stage electrodes 305 and the lower-stage electrodes 306, which are a plurality of insulated electrodes insulated from the upper-stage electrodes 304.

Furthermore, as shown in FIG. 11B, the opposite ends of the resistance pattern 307 on the heater member 3012 are connected to the middle-stage electrodes 305. The heater member 3012 is different from the heater member 3011 in this point. A total of four electrodes including the upper-stage electrodes 304 and the lower-stage electrodes 306 are electrically insulated from one another. Furthermore, the middle-stage electrodes 305 are electrically insulated from the upper-stage electrodes 304 and the lower-stage electrodes 306. Thus, on a front surface of the substrate with the middle-stage electrodes 305 disposed thereon, the heater member 3012 further comprises the upper-stage electrodes 304 and the lower-stage electrodes 306, which are a plurality of insulated electrodes insulated from the middle-stage electrodes 305.

Additionally, as shown in FIG. 11C, the opposite ends of the resistance pattern 307 on the heater member 3013 are connected to the lower-stage electrodes 306. The heater member 3013 is different from the heater member 3011 in this point. A total of four electrodes including the upper-stage electrodes 304 and the middle-stage electrodes 305 are electrically insulated from one another. Furthermore, the lower-stage electrodes 306 are electrically insulated from the upper-stage electrodes 304 and the middle-stage electrodes 305. Thus, on a front surface of the substrate with the lower-stage electrodes 306 disposed thereon, the heater member 3013 further comprises the upper-stage electrodes 304 and the middle-stage electrodes 305, which are a plurality of insulated electrodes insulated from the lower-stage electrodes 306.

Each of the heater members 3011, 3012, and 3013 is configured similarly to the heater member 300 according to the first and second embodiments, and comprises a substrate formed of alumina (not shown in the drawings), an insulating polyimide film (not shown in the drawings), and a backside electrode (not shown in the drawings). Furthermore, the backside electrode, the upper-stage electrodes 304, the middle-stage electrodes 305, and the lower-stage electrodes 306 each have a film configuration that can be stably subjected to soldering or wire bonding. Thus, as described above, the insulating polyimide film is formed in the entire area of the front surface except for the areas of the upper-stage electrodes 304, the middle-stage electrodes 305, and the lower-stage electrodes 306.

Additionally, according to the present embodiment, in FIG. 10, an upper side of the cutter guide groove 262a is referred to as an upper end of zones A, B, and C. A lower side of the cutter guide groove 262a is referred to as a lower end of zones A, B, and C.

In zone A, one heater member 3011 is disposed at the upper end, and one heater member 3013 is disposed at the lower end.

In zone B, one heater member 3012 is disposed at each of the upper end and the lower end.

In zone C, one heater member 3013 is disposed at the upper end, and one heater member 3011 is disposed at the lower end.

Here, for convenience of description, at the upper end, the heater member 3011 disposed in zone A is referred to as a heater member 301a, the heater member 3012 disposed in zone B is referred to as a heater member 301c, and the heater member 3013 disposed in zone C is referred to as a heater member 301e.

Furthermore, at the lower end, the heater member 3013 disposed in zone A is referred to as a heater member 301b, the heater member 3012 disposed in zone B is referred to as a heater member 301d, and the heater member 3013 disposed in zone C is referred to as a heater member 301f.

On the base end 266d side of the first high-frequency electrode 266, the connection chip 331a is formed at the upper end, and the connection chip 331b is formed at the lower end. Additionally, the relay chip 321 is formed at the bottom portion (leading end 266c side) of the first high-frequency electrode 266.

The connection chips 331a and 331b and the relay chip 321 are similar to the connection chips 331a and 331b and the relay chip 321 according to the second embodiment. However, the connection chips 331a and 331b and the relay chip 321 according to the third embodiment are different from the connection chips 331a and 331b and the relay chip 321 according to the second embodiment in that each of the connection chips 331a and 331b and the relay chip 321 according to the third embodiment comprises three electrodes.

Here, the electrodes disposed on the connection chip 331a are referred to as an electrode 339a, an electrode 339c, and an electrode 339e in this order from the top of FIG. 10. Furthermore, the electrodes disposed on the connection chip 331b are referred to as an electrode 339f, an electrode 339d, and an electrode 339b in this order from the top of FIG. 10. The electrode 339a, the electrode 339b, the electrode 339c, the electrode 339d, the electrode 339e, and the electrode 339f each have the same configuration as the configuration of the electrode 339.

Additionally, the electrodes disposed on the relay chip 321 are referred to as an electrode 325ab, an electrode 325cd, and an electrode 325ef in this order from the left of FIG. 10. Each of the electrode 325ab, the electrode 325cd, and the electrode 325ef has the same configuration as the configuration of the electrode 325.

The heater members 301a, 301b, 301c, 301d, 301e, and 301f, the connection chips 331a and 331b, and the relay chip 321 are joined to the first high-frequency electrode 266 by soldering.

In the connection chip 331a, the right ends, on FIG. 10, of the electrode 339a, the electrode 339c, and the electrode 339e are connected to the heater member energization lines 2681a, 2681c, and 2681e, respectively. Furthermore, in the connection chip 331b, the right ends, on FIG. 10, of the electrode 339b, the electrode 339d, and the electrode 339f are connected to the heater member energization lines 2681b, 2681d, and 2681f, respectively.

To control the heater members 301a and 301b in zone A, the heater member energization lines 2681a and 2681b are connected, via the cable 228, to the energy source 214, which is an external heating control device. Furthermore, to control the heater members 301c and 301d in zone B, the heater member energization lines 2681c and 2681d are connected, via the cable 228, to the energy source 214, which is an external heating control device. Additionally, to control the heater members 301e and 301f in zone C, the heater member energization lines 2681e and 2681f are connected, via the cable 228, to the energy source 214, which is an external heating control device.

Wiring routed from the connection chip 331a to the connection chip 331b along the substantial U shape of the first high-frequency electrode 226 is formed by connecting the electrodes on the adjacent heater members 301 together or connecting the electrode on the heater member 301 and the electrode on the relay chip 321 together, by the wires 351 and 353 for wire bonding.

Here, by way of example, the wiring for controlling the heater members 301a and 301b in zone A will be described.

The heater member energization line 2681a is connected to the base end 337a of the electrode 339a by soldering. The leading end 335a of the electrode 339a is connected to an upper-stage electrode 304-1 of the heater member 301e by the wire 353 for wire bonding. The upper-stage electrode 304-1 of the heater member 301e is connected to an upper-stage electrode 304-2 of the heater member 301e by the wire 353 for wire bonding. The upper-stage electrode 304-2 of the heater member 301e is connected to the upper-stage electrode 304-1 of the heater member 301c by the wire 353 for wire bonding. The upper-stage electrode 304-1 of the heater member 301c is connected to the upper-stage electrode 304-2 of the heater member 301c by the wire 353 for wire bonding. The upper-stage electrode 304-2 of the heater member 301c is connected to the upper-stage electrode 304-1 of the heater member 301a by the wire 351 for wire bonding. The upper-stage electrode 304-2 of the heater member 301a is connected, by the wire 351 for wire bonding, to one end of the electrode 325ab disposed on the relay chip 321.

Moreover, the heater member energization line 2681b is connected to the base end 337b of the electrode 339b by soldering. The leading end 335b of the electrode 339b is connected to a lower-stage electrode 306-1 of the heater member 301f by the wire 353 for wire bonding. The lower-stage electrode 306-1 of the heater member 301f is connected to a lower-stage electrode 306-2 of the heater member 301f by the wire 353 for wire bonding. The lower-stage electrode 306-2 of the heater member 301f is connected to the lower-stage electrode 306-1 of the heater member 301d by the wire 353 for wire bonding. The lower-stage electrode 306-1 of the heater member 301d is connected to the lower-stage electrode 306-2 of the heater member 301d by the wire 353 for wire bonding. The lower-stage electrode 306-2 of the heater member 301d is connected to the lower-stage electrode 306-1 of the heater member 301b by the wire 351 for wire bonding. The lower-stage electrode 306-2 of the heater member 301b is connected, by the wire 351 for wire bonding, to the other end of the electrode 325ab disposed on the relay chip 321.

This also applies to the connections by the wires 351 and 353 in zones B and C.

Thus, for example, the wire 351 connects the upper-stage electrode 304-1 disposed on the heater member 301a in zone A to the upper-stage electrode 304-2 disposed on the heater member 301c in zone B as shown in FIG. 10. Furthermore, for example, the wire 351 connects the lower-stage electrode 306-1 disposed on the heater member 301b in zone A to the lower-stage electrode 306-2 disposed on the heater member 301d in zone B as shown in FIG. 10.

Additionally, as shown in FIG. 10 and FIG. 11A, the wire 353 connects the middle-stage electrode 305-1 disposed on the heater member 301a in zone A to the middle-stage electrode 305-2 disposed on the heater member 301a in zone A. The wire 353 connects the middle-stage electrode 305-1 disposed on the heater member 301a in zone A to the middle-stage electrode 305-2 disposed on the heater member 301c in zone B. In addition, as shown in FIG. 10 and FIG. 11A, the wire 353 connects the lower-stage electrode 306-1 disposed on the heater member 301a in zone A to the lower-stage electrode 306-2 disposed on the heater member 301a in zone A and to the lower-stage electrode 306-2 disposed on the heater member 301c in zone B.

Furthermore, as shown in FIG. 10 and FIG. 11A, the wire 353 connects the upper-stage electrode 304-1 disposed on the heater member 301b in zone A to the upper-stage electrode 304-2 disposed on the heater member 301b in zone A and to the upper-stage electrode 304-2 disposed on the heater member 301d in zone B. Additionally, as shown in FIG. 10 and FIG. 11A, the wire 353 connects the middle-stage electrode 305-1 disposed on the heater member 301b in zone A to the middle-stage electrode 305-2 disposed on the heater member 301b in zone A, and connects the middle-stage electrode 305-1 disposed on the heater member 301b in zone A to the middle-stage electrode 305-2 disposed on the heater member 301d in zone B.

In addition, as shown in FIG. 10 and FIG. 11A, for example, the wire 353 electrically connects, by wire bonding, the lower-stage electrode 306-1 disposed on the heater member 301e in zone C and the upper-stage electrode 304-1 and middle-stage electrode 305-1 disposed on the heater member 301e in zone C to the heater member energization lines 2681a, 2681c, and 2681e.

In the connections by the wires 351 and 353 in zone A, the wires 351 and 353 may be looped on the heater members 301e, 301c, 301d, and 301f and on the first high-frequency electrode 266.

Thus, like the second embodiment, the present embodiment can control, even with increased number of zones, the heater members 300 in each zone independently of the heater members 300 in the other zones and thus carry out the treatment of the living tissue in each zone independently of the treatment of the living tissue in the other zones. The control for each zone according to the present embodiment may be performed based on the amount by which the pedal 216a of the foot switch 216 is depressed or using the switch (not shown in the drawings) disposed in the energy source 214.

Furthermore, the present embodiment provides a wiring path between the heater member energization line 2681a and the heater member energization line 2681b on which path the resistance patters 307 on the heater member 301a and heater member 301b arranged in zone A are connected together in series along the substantial U shape of the first high-frequency electrode 266. Additionally, in this case, the present embodiment uses the heater members 301c, 301d, 301e, and 301f and the electrode 325ab of the relay chip 321 in zone B and zone C as relay electrodes.

Thus, even with the connections by the wires 351 and 353 for wire bonding, the present embodiment can prevent an increase in wire length which is the sum of the lengths of the wires 351 and 353. Hence, the present embodiment can form stable wiring with the height of the wires 351 and 353 reduced. The height of the wires 351 and 353 is indicative of the height of the wires 351 and 353 in the direction of height of the first high-frequency electrode 266. The direction of height of the first high-frequency electrode 266 is orthogonal to a plane on which the heater member 301a and the like are arranged.

Furthermore, according to the present embodiment, the opposite ends of the heater members 300 are connected together by wire bonding using the wires 351 and 353, enabling a reduction in the length of the wires 351 and 353 between the heater members 300 located in proximity (for example, the heater member 301a and the heater member 301c).

In this regard, the electrodes 304, 305, and 306 used as relay electrodes in the heater member 300 may be short-circuited between the opposite ends of each of the electrodes 304, 305, and 306. However, this short-circuit wiring may limit the area in which the resistance pattern 307 is formed, making the heat generation in the heater member 300 less uniform. Thus, the wires 351 and 353 for wire bonding which are looped on the heater member 300 are desirably used as in the case of the present embodiment.

The wiring of the heater members 301a and 301b in zone A has been described. As shown in FIG. 10 and FIG. 11B, the wiring for controlling the heater members 301c and 301d in zone B connects, by the wires 351 and 353 for wire bonding, the heater member energization line 2681c, the electrode 339c, the middle-stage electrode 305 disposed on the heater member 301e, the middle-stage electrode 305 and resistance pattern 307 disposed on the heater member 301c, the middle-stage electrode 305 disposed on the heater member 301a, the electrode 325cd disposed on the relay chip 321, the middle-stage electrode 305 disposed on the heater member 301b, the middle-stage electrode 305 and resistance pattern 307 disposed on the heater member 301d, the middle-stage electrode 305 disposed on the heater member 301f, the electrode 339d, and the heater member energization line 2681d together. Here, between the heater member energization lines 2681b and 2681c, the resistance patterns 307 on the heater members 301c and 301d in zone B are connected together in series.

Furthermore, the wiring for controlling the heater members 301e and 301f in zone C connects, by the wires 351 and 353 for wire bonding, the heater member energization line 2681e, the electrode 339e, the lower-stage electrode 306 and resistance pattern 307 disposed on the heater member 301e, the lower-stage electrode 306 disposed on the heater member 301c, the lower-stage electrode 306 disposed on the heater member 301a, the electrode 325ef disposed on the relay chip 321, the upper-stage electrode 304 disposed on the heater member 301b, the upper-stage electrode 304 disposed on the heater member 301d, the upper-stage electrode 304 and resistance pattern 307 disposed on the heater member 301f, the electrode 339f, and the heater member energization line 2681f together. Here, between the heater member energization lines 2681e and 2681f, the resistance patterns 307 on the heater members 301e and 301f in zone C are connected together in series.

Additionally, according to the present embodiment, the wires 351 and 353, which interconnect the heater members 300, are looped on the heater members 300 as seen in FIG. 10. Thus, the many wires 351 and 353 can be formed in juxtaposition in the narrow zones A, B, and C.

In addition, the present embodiment forms three zones A, B, and C, and forms three lines of wiring on the heater member 300 so as to separately control the heater members 300 in each zone. However, according to the present embodiment, even if the number of zones is increased and as many wires as the zones are installed, the width of the zone, required for the formation of wiring, is prevented from being increased. Thus, the present embodiment can provide a narrow first holding member 262 even if the heater members 300 are controlled using an increased number of zones. Consequently, the present embodiment can separately control the heater members 300 in each zone, allowing a reduction in the size of the holding section 226.

The present invention is not limited to the above-described embodiments proper. In practice, the present invention can be embodied with the components of the above-described embodiments modified without departing from the spirit of the present invention. Furthermore, various inventions can be formed by combining a plurality of the components disclosed in the above-described embodiments.

What is claimed is:

1. A surgical treatment system for allowing energy generated by an energy source to act on living tissue to treat the living tissue, the treatment system comprising:
  a pair of holding members adapted to hold living tissue by moving at least one of the holding members relative to the other holding member;
  a plurality of heating members disposed on at least one of the holding members and disposed discretely from one another;
  a heat-generating heat transmission pattern disposed on the respective heating members to transfer heat to the living tissue held by the holding members;
  a pair of electrodes disposed at opposite ends of the heat-generating heat transmission pattern on each of the heating members to generate heat based on energy supplied to the heat-generating heat transmission pattern;
  wires each electrically connecting one of the heating members to another heating member by wire bonding; and
  an energization line connected to one of the wires and to an energy source adapted to supply the energy from the energy source to the electrodes on the heating member via the wire,
  wherein the heating members each comprise one or more insulated electrodes electrically insulated from the pair of electrodes and provided on a plane of the heating members on which the pair of electrodes are disposed, and the insulated electrodes are used as a relay section for connection of the wires.

2. The surgical treatment system according to claim 1, wherein the heating members are divided into a plurality of groups, each of the wires electrically connects, by wire bonding, one of the pair of electrodes disposed on each of the heating members in a first group, to the insulated electrode disposed on the corresponding one of the heating members in a second group, and electrically connects, by wire bonding, the insulated electrode disposed on each of the heating members in the first group, to one of the pair of electrodes disposed on the corresponding one of the heating members in the second group, and the energization line supplies the energy via the wires to the electrodes disposed on the heating members in the first group and the second group to separately supply the energy to the heating members in each of the groups.

3. The surgical treatment system according to claim 2, wherein each of the wires electrically connect, by wire bonding, the insulated electrode disposed on each of the heating members in the second group and the other electrode disposed on the corresponding one of the heating members in the second group to the energization line.

4. The surgical treatment system according to claim 1, wherein the heating members are divided into a plurality of groups, one of the wires connects one of the pair of electrodes disposed on the heating members in a first group to one of the insulated electrodes disposed on the heating members in a second group, and another of the wires connects one of the insulated electrodes disposed on the heating members in the first group to at least one other insulated electrode disposed on the heating members in the first group and the other insulated electrode disposed on the heating members in the second group.

5. The surgical treatment system according to claim 4, wherein the wire electrically connects the other of the pair of electrodes disposed on each of the heating members in the first group and the other insulated electrode disposed on the heating members in the first group to the energization line by wire bonding.

* * * * *